(12) United States Patent
Hartmann et al.

(10) Patent No.: US 8,644,570 B2
(45) Date of Patent: Feb. 4, 2014

(54) SYSTEM AND METHOD FOR AUTOMATIC REGISTRATION BETWEEN AN IMAGE AND A SUBJECT

(75) Inventors: Steven L. Hartmann, Superior, CO (US); Robert Teichman, Lafayette, CO (US); Laurent Verard, Andover, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 13/567,606

(22) Filed: Aug. 6, 2012

(65) Prior Publication Data

US 2012/0294491 A1 Nov. 22, 2012

Related U.S. Application Data

(62) Division of application No. 12/465,206, filed on May 13, 2009, now Pat. No. 8,238,631.

(51) Int. Cl.
*G06K 9/00* (2006.01)

(52) U.S. Cl.
USPC ............ 382/128; 382/276; 600/407; 600/414

(58) Field of Classification Search
USPC ........................ 382/276, 128; 600/407, 414
See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 5,983,126 A | 11/1999 | Wittkampf | |
| 6,474,341 B1 | 11/2002 | Hunter et al. | |
| 6,609,022 B2 | 8/2003 | Vilsmeier et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,570,791 B2 | 8/2009 | Frank et al. | |
| 7,751,865 B2 | 7/2010 | Jascob et al. | |
| 7,899,226 B2 | 3/2011 | Pescatore et al. | |
| 8,503,745 B2 | 8/2013 | Simon et al. | |
| 2004/0019265 A1 | 1/2004 | Mazzocchi et al. | |
| 2004/0030236 A1 | 2/2004 | Mazzocchi et al. | |
| 2004/0030237 A1* | 2/2004 | Lee et al. ...................... | 600/414 |
| 2004/0167391 A1 | 8/2004 | Solar et al. | |
| 2004/0167393 A1 | 8/2004 | Solar et al. | |

(Continued)

FOREIGN PATENT DOCUMENTS

EP 1561423 A1 8/2005

OTHER PUBLICATIONS

"AxiEM Electromagetic Navigation," tri-fold brochure, Medtronic Navigation (2005) 2 pages.

(Continued)

*Primary Examiner* — Joseph Chang
(74) *Attorney, Agent, or Firm* — Harness, Dickey

(57) ABSTRACT

A patient defines a patient space in which an instrument can be tracked and navigated. An image space is defined by image data that can be registered to the patient space. A tracking device can be connected to a member in a known manner that includes imageable portions that generate image points in the image data. The tracking device can be tracked to register patient space to image space.

21 Claims, 6 Drawing Sheets

(56) References Cited

U.S. PATENT DOCUMENTS

| | | |
|---|---|---|
| 2004/0199072 A1 | 10/2004 | Sprouse et al. |
| 2007/0225599 A1 | 9/2007 | Solar et al. |
| 2008/0242978 A1 | 10/2008 | Simon et al. |
| 2009/0005668 A1 | 1/2009 | West et al. |
| 2009/0022266 A1 | 1/2009 | Stayman et al. |
| 2009/0257551 A1 | 10/2009 | Dafni et al. |
| 2010/0020926 A1 | 1/2010 | Boese et al. |
| 2010/0063388 A1 | 3/2010 | Solar et al. |
| 2010/0217120 A1 | 8/2010 | Solar et al. |
| 2010/0290690 A1 | 11/2010 | Hartmann et al. |
| 2011/0071389 A1 | 3/2011 | Simon et al. |
| 2012/0201421 A1 | 8/2012 | Hartmann et al. |

OTHER PUBLICATIONS

"Solutions for Improved Surgeries, Navigation and Intra-Operative Imaging." Jul. 2007. Medtronic Navigation. pp. 1-21.

"Treon, StealthStation," brochure, Medtronic Surgical Navigation Technologies (2001) 8 pages.

International Search Report and Written Opinion mailed Jan. 18, 2012 for PCT/US2011/057204 claiming benefit of U.S. Appl. No. 12/910,445, filed Oct. 22, 2010.

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).

* cited by examiner

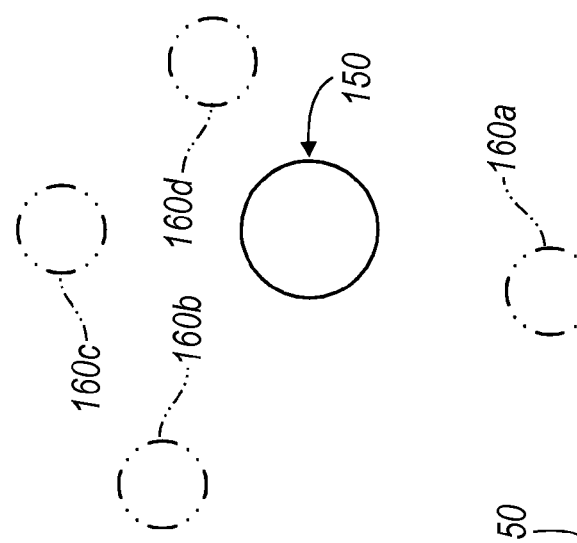
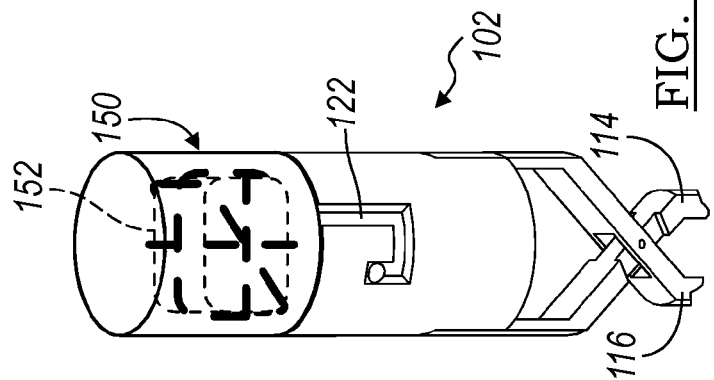
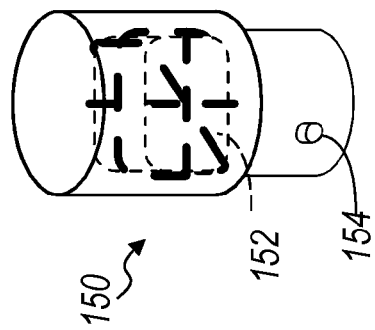
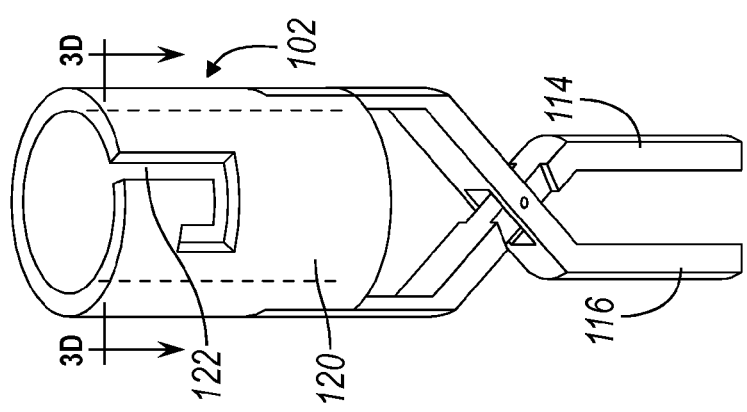
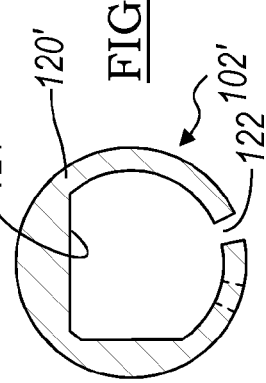

SYSTEM AND METHOD FOR AUTOMATIC REGISTRATION BETWEEN AN IMAGE AND A SUBJECT

CROSS REFERENCE TO RELATED APPLICATIONS

This application is a divisional of U.S. patent application Ser. No. 12/465,206 filed on May 13, 2009. The disclosure of the above application is incorporated herein by reference.

FIELD

The subject disclosure is related generally to an operative procedure and particularly to registration of image space to subject space.

BACKGROUND

This section provides background information related to the present disclosure which is not necessarily prior art.

An instrument can be navigated relative to a subject for performing various procedures. For example, a subject can include a patient on which a surgical procedure is being performed. During a surgical procedure, an instrument can be tracked in a subject space, also referred to as patient space. The location of the instrument that is tracked can be displayed on the display device relative to an image of the patient.

The position of the patient can be determined with a tracking system. Generally, a patient is registered to the image, via tracking an instrument relative to the patient to generate a translation map between the patient space and the image space. This often requires time during a surgical procedure for a user, such as a surgeon, to identify one or more points in the subject space and correlating, often identical points, in the image space.

a. Only after registration can the position of the instrument be appropriately displayed on the display device. The position of the instrument relative to the subject can be displayed as an icon on the display device.

SUMMARY

This section provides a general summary of the disclosure, and is not a comprehensive disclosure of its full scope or all of its features.

The tracking of an instrument during a procedure, such as a surgical or operative procedure, allows for navigation of a procedure. When image data is used to define an image space it can be correlated or registered to a physical space defined by a subject, such as a patient. According to various embodiments, therefore, the patient defines a patient space in which an instrument can be tracked and navigated. The image space defined by the image data can be registered to the patient space defined by the patient. The registration can occur with the use of fiducials that can be identified in the image data and in the patient space.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 3A-4C are plan views of an imageable and trackable device, according to various embodiments;

Corresponding reference numerals indicate corresponding parts throughout the several views of the drawings.

DETAILED DESCRIPTION

Example embodiments will now be described more fully with reference to the accompanying drawings.

Figure 1:
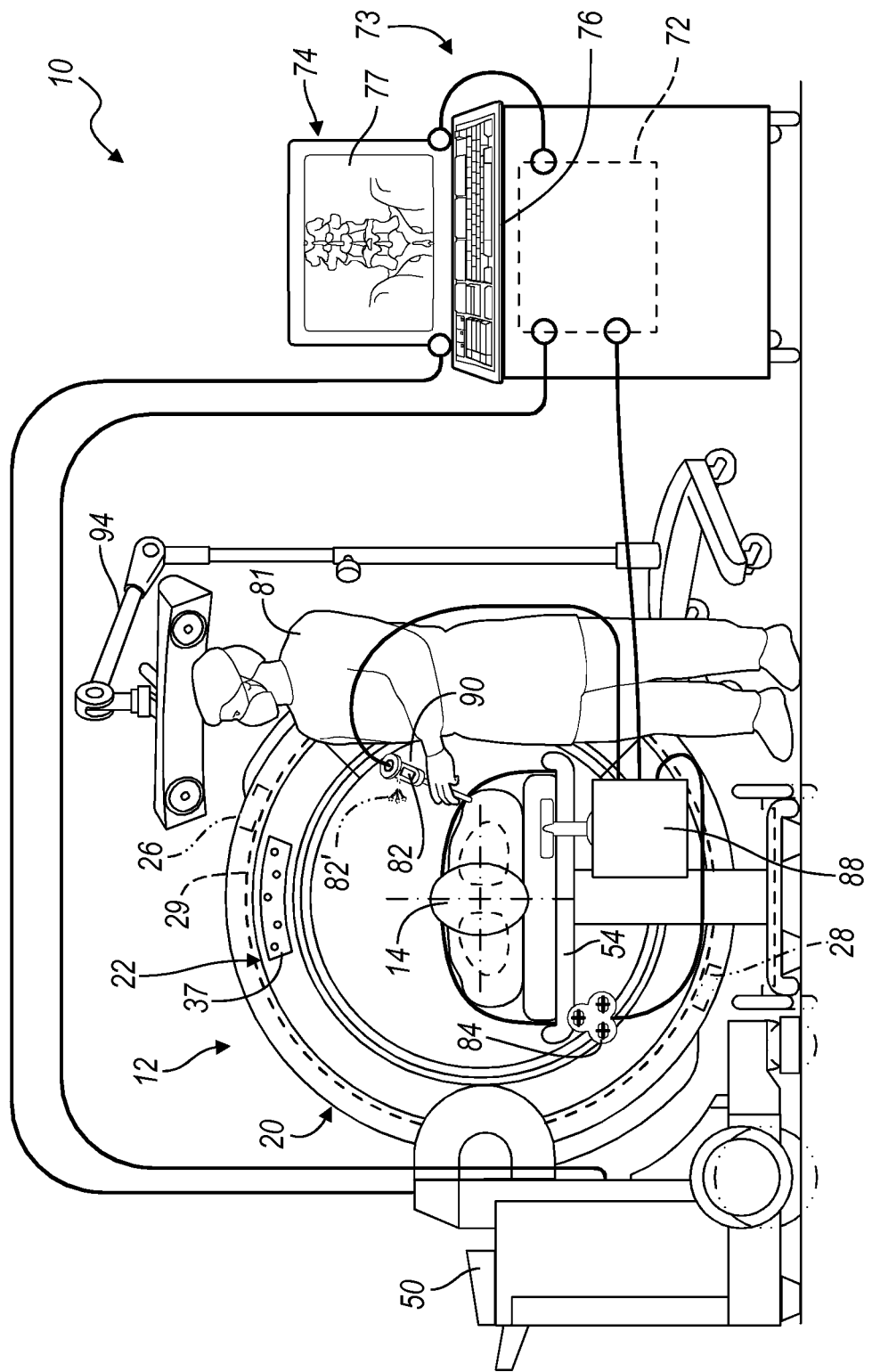
FIG. 1 is diagrammatic view illustrating an overview of a navigation system, according to various embodiments.
Figure 2:
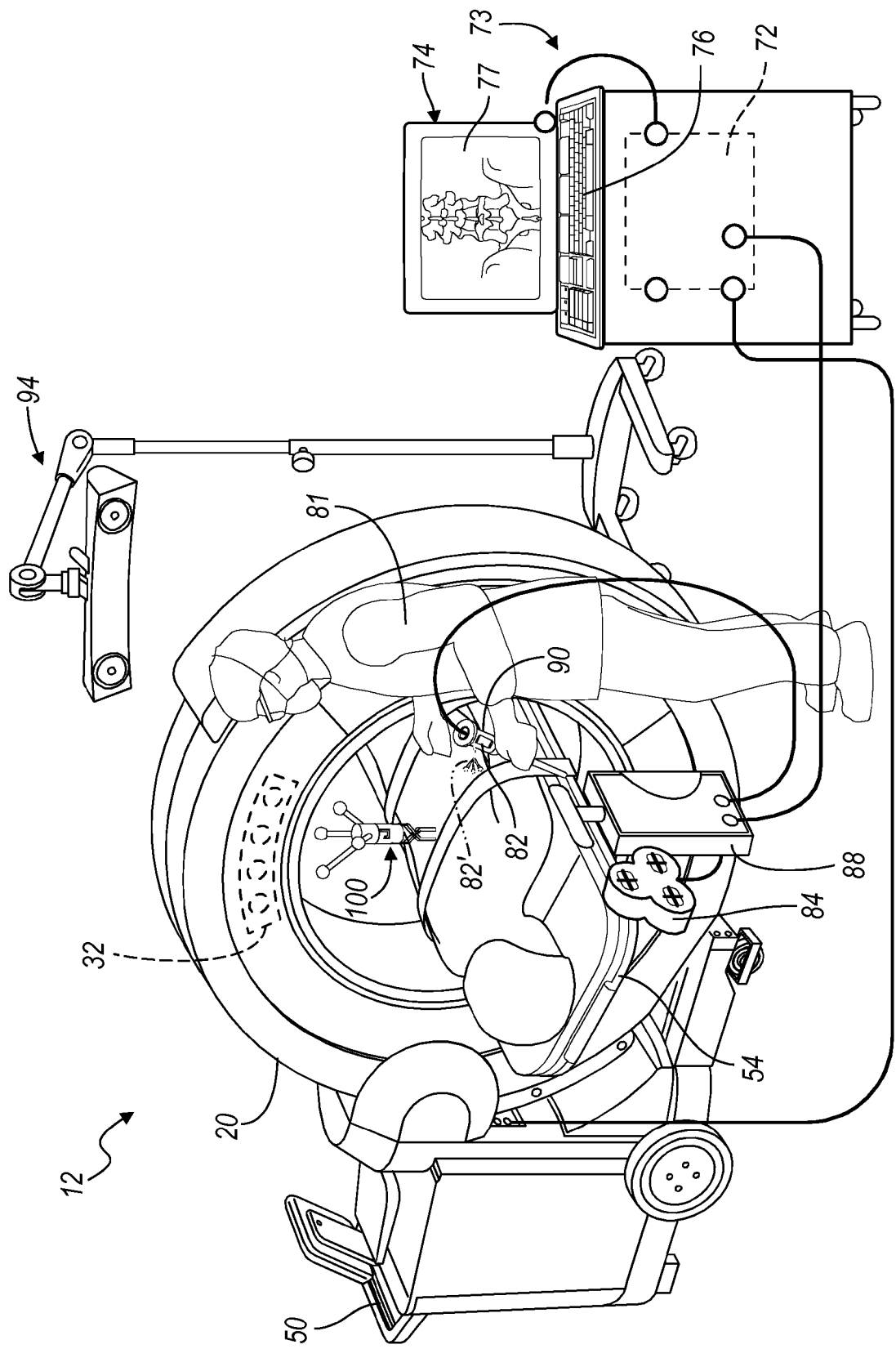
FIG. 2 is diagrammatic alternative view of the system of FIG. 1, according to various embodiments.

FIGS. 1 and 2 are diagrammatic views illustrating an overview of a navigation system 10 that can be used for various procedures. The navigation system 10 can be used to track the location of an implant, such as a spinal implant or orthopedic implant, relative to a patient 14. Also, the navigation system 10 can track the position and orientation of an instrument 90, such as a biopsy needle or resection instrument. It should further be noted that the navigation system 10 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 10 and the various instruments may be used in any appropriate procedure, such as one that is generally minimally invasive or an open procedure.

The navigation system 10 includes an imaging device 12 that is used to acquire pre-, intra-, or post-operative or real-time image data of a subject, such as a patient 14. It will be understood, however, that any appropriate subject can be imaged and any appropriate procedure may be performed relative to the subject. In the example shown, the imaging device 12 comprises an O-arm® imaging device sold by Medtronic Navigation, Inc. having a place of business in Louisville, Colo., USA. The imaging device 12 may have a generally annular gantry housing 20 and an image capturing portion 22. The image capturing portion 22 may include an x-ray source or emission portion 26 and an x-ray receiving or image receiving portion 28 located generally or as practically possible 180 degrees from each other and mounted on a rotor (not illustrated) relative to a track or rail 29. The image capturing portion 22 can be operable to rotate 360 degrees during image acquisition. The image capturing portion 22 may rotate around a central point or axis, allowing image data of the patient 14 to be acquired from multiple directions or in multiple planes. The imaging device 12 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 12 can utilize flat plate technology having a 1,720 by 1,024 pixel viewing area.

The position of the image capturing portion 22 can be precisely known relative to any other portion of the imaging device 12. The imaging device 12, according to various embodiments, can know and recall precise coordinates relative to a fixed or selected coordinate system. This can allow the imaging system 12 to know its position relative to the patient 14 or other references. In addition, as discussed herein, the precise knowledge of the position of the image capturing portion 22 can be used in conjunction with a tracking system to determine the position of the image capturing portion 22 and the image data relative to the tracked subject, such as the patient 14.

The imaging device 12 can also be tracked with a tracking device 37. The image data defining an image space acquired of the patient 14 can, according to various embodiments, be inherently or automatically registered relative to a patient space of the patient 14 in the navigation system 10. The automatic registration can be achieved by including the tracking device 37 on the imaging device 12 and/or the determinable precise location of the image capturing portion 22. According to various embodiments, as discussed herein, imageable portions, virtual fiducial points and other features can also be used to allow for registration, automatic or otherwise. It will be understood, however, that image data can be acquired of any subject which will define subject space. Patient space is an exemplary subject space. Registration allows for a translation between patient space and image space.

The patient 14 can also be tracked or fixed within the navigation system 10 to allow for registration. As discussed further herein, registration of the image space to the patient space or subject space allows for navigation of the instrument 90 with the image data. When navigating the instrument 90, a position of the instrument 90 can be illustrated relative to image data acquired of the patient 14 on a display device 74. Various tracking systems, such as one including an electromagnetic (EM) localizer 84 or an optical localizer 94 can be used to track the instrument 90.

More than one tracking system can be used to track the instrument 90 in the navigation system 10. According to various embodiments, these can include an electromagnetic tracking (EM) system having an EM localizer 84 and an optical tracking system having an optical localizer 94. Either or both of the tracking systems can be used to tracked selected tracking devices, as discussed herein. It will be understood, unless discussed otherwise, that a tracking device can be a portion trackable with a selected tracking system. A tracking device need not refer to the entire member or structure to which the tracking device is affixed or associated.

It is appreciated, however, that an imaging device other than the imaging device 12, such as a fluoroscopic C-arm can be used. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging systems can also include MRI, CT, ultrasound, etc.

An imaging device controller 50 that may control the imaging device 12 can receive the image data generated at the image capturing portion 22 and store the images for later use. The controller 50 can also control the rotation of the image capturing portion 22 of the imaging device 12. It will be understood that the controller 50 need not be integral with the processing unit or processing portion 36 and may include a second and separate processor, such as that in a portable computer.

The patient 14 can be fixed onto an operating table 54. According to one example, the table 54 can be an Axis Jackson® operating table sold by OSI, a subsidiary of Mizuho Ikakogyo Co., Ltd., having a place of business in Tokyo, Japan or Mizuho Orthopedic Systems, Inc having a place of business in California, USA. Patient positioning devices can be used with the table, and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated by reference.

The position of the patient 14 relative to the imaging device can be determined by the navigation system 10. The tracking device 37 can be used to track and locate at least a portion of the imaging device 12, for example the housing 20. The patient 14 can be tracked with a tracking device, such as one used as a dynamic reference frame, as discussed further herein. Accordingly, the position of the patient 14 relative to the imaging device 12 can be determined. Further, the location of the imaging portion 22 can be determined relative to the housing 20 due to its precise position on the rail 29 within the housing 20, substantially inflexible rotor, etc. The imaging device 12 can include an accuracy of within 10 microns, for example, if the imaging device 12 is an O-Arm® imaging device sold by Medtronic Navigation, Inc. having a place of business in Louisville, Colo. Precise positioning of the imaging portion 22 is further described in U.S. Pat. Nos. 7,188, 998; 7,108,421; 7,106,825; 7,001,045; and 6,940,941; all of which are incorporated herein by reference, In operation, the imaging device 12 can generate and/or emit x-rays from the x-ray source 26 that propagate through the patient 14 and are received by the x-ray imaging receiving portion 28. The image capturing portion 22 generates image data representing the intensities of the received x-rays. Typically, the image capturing portion 22 can include an image intensifier that first converts the x-rays to visible light and a camera (e.g. a charge couple device) that converts the visible light into digital image data. The image capturing portion 22 may also be a digital device that converts x-rays directly to digital image data for forming images, thus potentially avoiding distortion introduced by first converting to visible light.

Two dimensional and/or three dimensional fluoroscopic image data that may be taken by the imaging device 12 can be captured and stored in the imaging device controller 50. Multiple image data taken by the imaging device 12 may also be captured and assembled to provide a larger view or image of a whole region of a patient 14, as opposed to being directed to only a portion of a region of the patient 14. For example, multiple image data of the patient's 14 spine may be appended together to provide a full view or complete set of image data of the spine.

The image data can then be forwarded from the image device controller 50 to a navigation computer and/or processor 72 that can be a part of a controller or work station 73 having the display 74 and a user interface 76. It will also be understood that the image data is not necessarily first retained in the controller 50, but may also be directly transmitted to the work station 73. The work station 73 can provide facilities for displaying the image data as an image 77 on the display 74, saving, digitally manipulating, or printing a hard copy image of the received image data. The user interface 76, which may be a keyboard, mouse, touch pen, touch screen or other suitable device, allows a user 81 to provide inputs to control the imaging device 12, via the image device controller 50, or adjust the display settings of the display 74. The work station 73 may also direct the image device controller 50 to adjust the image capturing portion 22 of the imaging device 12 to obtain various two-dimensional images along different planes in order to generate representative two-dimensional and three-dimensional image data.

With continuing reference to FIG. 1, the navigation system 10 can further include a tracking system such as an electromagnetic (EM) navigation tracking system. The EM tracking system can include a localizer, such as a transmitter coil array 84. The EM tracking system can also include an EM controller and interface portion 88 and a tracking device 82 associated with the instrument 90. The EM controller 88 can be connected to the processor portion 72, which can include a processor included within a computer. The localizer or transmitter coil array 84 can be attached directly to the image device 12, attached to the OR table 54, or any other appropriate location. The EM tracking system may include the STEALTHSTATION® AXIEM™ Navigation System, sold by Medtronic Navigation, Inc. having a place of business in Louisville, Colo.; or can be the EM tracking system described in U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the tracking system 82 may also be or include any appropriate tracking system, including a STEALTHSTATION® TREON® or S7™ tracking systems having an optical localizer, similar to the optical localizer 94, and sold by Medtronic Navigation, Inc. of Louisville, Colo. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 12, etc. Alternatively, various portions, such as the instrument 90, may employ a wireless communications channel, such as that disclosed in U.S. Pat. No. 6,474,341, entitled "Surgical Communication Power System," issued Nov. 5, 2002, herein incorporated by reference, as opposed to being coupled directly to the EM controller 88. Also, the tracking device 82 can generate a field sensed by the coil array 84 to track the tracking device 82.

Various portions of the navigation system 10, such as the instrument 90, and others as will be described in detail below, can be equipped with at least one, and generally multiple, of the tracking devices 82. The instrument can also include more than one type or modality of tracking device, such as the EM tracking device 82 and an optical tracking device 82'. The instrument 90 can include a graspable or manipulable portion at a proximal end and the tracking devices 82, 82' may be fixed near the manipulable portion of the instrument 90.

Additional representative or alternative localization and tracking system is set forth in U.S. Pat. No. 5,983,126, entitled "Catheter Location System and Method," issued Nov. 9, 1999, which is hereby incorporated by reference. The navigation 10 system may be a hybrid system that includes components from various tracking systems.

According to various embodiments, the navigation system 10 can be used to track the instrument 90 relative to the patient 14. The instrument 90 can be tracked with the tracking system, as discussed above. Image data of the patient 14, or an appropriate subject, can be used to assist the user 81 in guiding the instrument 90. The image data, however, is registered to the patient 14. The image data defines an image space that is registered to the patient space defined by the patient 14. The registration can be performed as discussed herein, automatically, manually, or combinations thereof.

Generally, registration allows a translation map to be generated of the physical location of the instrument 90 relative to the image space of the image data. The translation map allows the tracked position of the instrument 90 to be displayed on the display device 74 relative to the image data 77. An icon 90i (FIGS. 5 and 8) can be used to illustrate the location of the instrument relative to the image data 77.

Figure 3B:
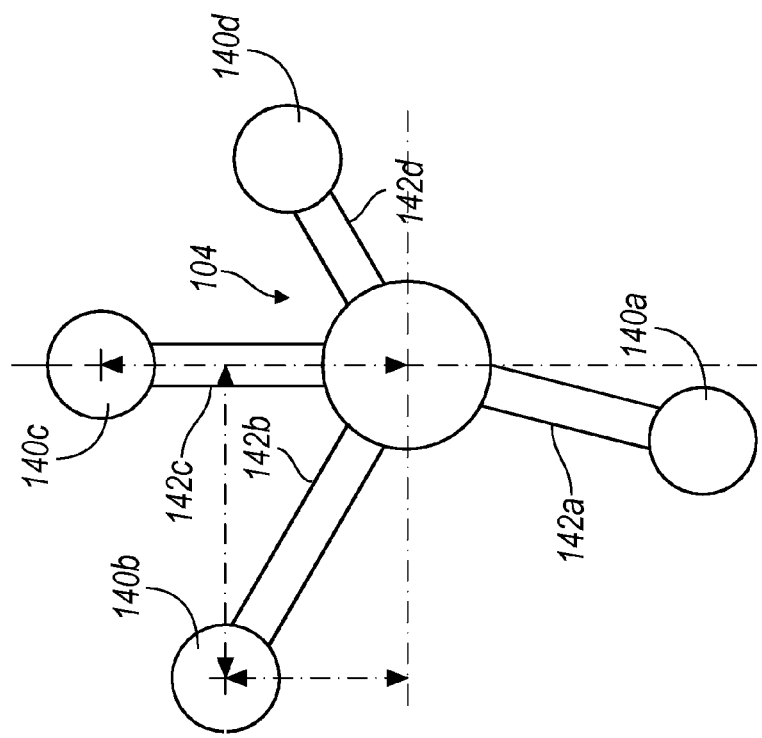
Figure 3A:
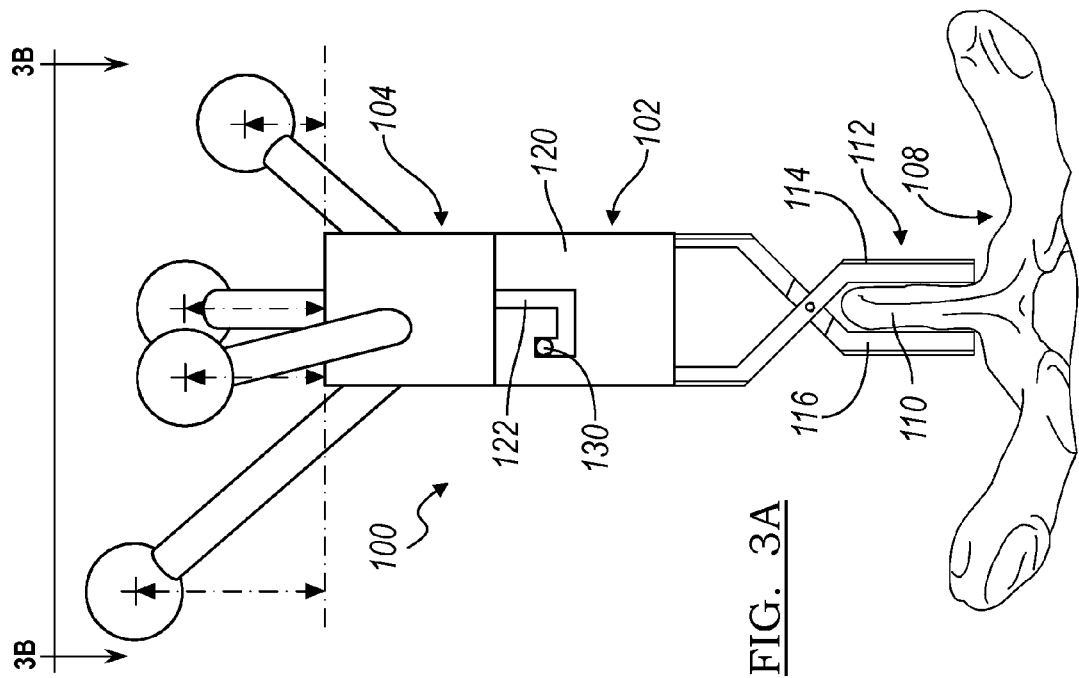

A registration system or method can use a fiducial assembly 100, is illustrated in FIGS. 3A and 3B. The fiducial assembly 100 can include a clamp or other fixation portion 102 and an imageable fiducial body 104. The fixation portion 102 can be provided to fix any appropriate portion, such as a portion of the anatomy. As illustrated in FIGS. 1 and 2, the fiducial assembly 100 can be interconnected with a portion of a spine 108 such as a spinous process 110.

The fixation portion 102 can be interconnected with a spinous process 110 in any appropriate manner. For example, a pin or a screw can be driven into the spinous process 110. Alternatively, or in addition thereto, a clamp portion 112 can be provided to interconnect the spinous process 110. A first clamp leg 114 and a second clamp leg 116 can be driven or moved together to bind or fixedly connect with the spinous process 110. The movement of the clamping legs 114, 116 can be in any appropriate manner.

The fixation member 112 can further include a seat or seat body 120. The seat body 120 can include a key groove or locking portion 122, which can be defined as a J-groove 122. The J-groove 122 can terminate at an opening at the top of the seat portion 120, as illustrated in FIG. 3C. A locking portion or extension, as discussed herein, can cooperate with the J-groove 122 to hold a member relative to the seat 120. Any portion being held relative to the seat 120 can include a resilient member to move the locking portion into the tip or locking region 122a of the J-groove 122. When a locking portion is within the locking region 122a, the member positioned relative to the seat 120 is positioned at a known and fixed location relative to the seat 120. This can be used for repeatedly placing a member relative to the base 102 or a subject, such as the patient 14.

With reference to FIG. 3D, an alternative seat body 120' is illustrated. The alternative seat body 120' can be a portion of an alternative base portion or fixation member 102. The alternative seat body 120' can include a flat or keyed portion 124. A member positioned relative to the alternative seat portion 120' can be positioned relative to the seat portion 120 in a known configuration due to the keyed configuration which allows only a limited number of rotational positions of the member. It will be understood that a locking groove, such as the locking groove 122, can also be provided in conjunction with the keyed walls 124.

The fixation member 102, 102' can be fixed to a subject, such as the patient 14. With the keyed or fixation grooves or portions, a member positioned relative to the fixation base 102 can be positioned in a known and fixed position. The keyed walls 124 or the J-groove 122 can rotationally and axially hold a member relative to the fixation base 102. As discussed further herein, this can fix a member in three dimensional space relative to the subject to which the base 102 is fixed and assists in defining at least six degrees of freedom relative to the subject.

The imageable body 104 can be interconnected with the seat body 120 by including a connection portion that can define a key interaction portion or rod 130. It will be further understood that the imageable portion 104 can also include a configuration to cooperate or interact with the polygonal sides 124 of the seat body 120', as illustrated in FIG. 3D. As discussed further herein, the interconnection, either or both with the key slot 122 or the polygonal portion 124, allows for the imageable body 104 to be positioned relative to the fixation member 102 in a substantially repeatable and in a known configuration.

The imageable body 104 can include one or more imageable sections or portions, such as a first imageable portion 140a, a second imageable portion 140b, a third imageable portion 140c, and a fourth imageable portion 140d. It will be understood that the imageable portions 140a-140d can include regions defined substantially only by a spherical portion at an end of extensions 142a-142d, the entire imageable body 104 can be imageable, or any selected portion thereof. For example, if only the spheres of the imageable portions 140a-140d are imageable, the image acquired of the imageable body 104 can include only images of four points defined by the imageable portions 140a-140d. It will be understood, however, that any appropriate imageable configuration can be defined by the imageable body 104, such as providing portions of the extension arms 142a-142d that are also imageable. The discussion herein to the imageable portions 140a-140d is for simplicity of the current discussion.

As discussed above, the imageable body 104 can be positioned or fixed relative to the fixation body 102 and in a known and selected manner. Accordingly, each of the imageable portions 140a-140d can be positioned at a fixed and different location in three dimensional space. Each of the imageable portions 140a-140d can include a center 140an-140dn. Each of the centers 140an-140dn can be positioned at a selected and different heights Za-Zd relative to a Z axis Z. The centers 140an-140dn can be further positioned relative to X and Y axes at known locations Xa, Ya-Xd, Yd. Accordingly, each of the imageable portions 140a-140d can include a center positioned at known and different three dimensional locations Xa, Ya, Za-Xd, Yd, Zd. When each of the centers 140an-140dn include a different three dimensional location, the information in the image data, as discussed further herein, also includes different three dimensional locations and allows for identification of multiple points in three dimensional space for registration.

When the imageable portions 140a-140d are imaged with the imaging device 12, image data is generated that includes or identifies the imageable portions 140a-140d. As discussed further herein, the imageable portions 140a-140d can be identified in image data automatically, such as with a processor executing a program, manually, or combinations thereof. Methods of automatic imageable portion identification include those disclosed in U.S. Patent Application Publication No. 2008/0242978, (U.S. patent application Ser. No. 11/693,558) filed on Mar. 29, 2007, incorporated herein by reference. Manual identification can include selecting a center or region in the image data wherein the imageable portion has been imaged. Regardless, the imageable portions 140a-140d identified in the image data can be used as fiducial points or positions that can be used to register the image data or the image space of the image data with patient space.

With reference to FIGS. 4A and 4B, a tracking device 150 is illustrated. The tracking device 150 can be tracked with any appropriate tracking system, such as an EM tracking system. The tracking device 150 can include an electromagnetic coil or coil array portion 152. It will be understood, however, that the tracking device 150 can include any appropriate tracking device. For example, the tracking device 150 can include an optical tracking portion, an acoustic tracking portion, or any other appropriate tracking portion. Further, the tracking device 150 can transmit, receive, or combinations thereof a signal or radiation for tracking the tracking device 150.

The tracking device 150 can further include a peg or rod 154 that is operable to interconnect with the groove portion 122 of the base 102, as specifically illustrated in FIG. 4B. The tracking device 150 can further include portions that cooperate with the keyed flats 124 of the alternative base 102′, illustrated in FIG. 3D. Accordingly, the tracking device 150 can be connected with the fixation base 102 in a manner that is in a substantially similar or identical and/or known orientation and position relative to the base 102 as the imageable body 104. In this manner, the tracking device 150 can be connected with the mounting base 102 in a known configuration and orientation. The tracking device 150 can therefore be tracked relative to any portion, such as the spinal process 110 to which the base 102 is connected.

The tracking device 150 can be calibrated relative to the mounting base 102 to provide information or orientation coordinates. For example, the tracking device 150 can be calibrated to identify or located four virtual points 160a-160d. Each of the virtual points 160a-160d can include or define a center 160an-160dn. Each of the virtual points 160a-160d or the centers thereof 160an-160dn can include three dimensional coordinates that substantially correspond or are identical to the X, Y and Z coordinates Xa, Ya, Za-Xd, Yd, Zd. Accordingly, the virtual points 160a-160d can substantially overlay or be positioned in space at the same physical locations as the imageable portions 140a-140d. Because the tracking device 150 can be interconnected with the fixation base 102 in a known manner, the tracking device and the virtual points 160a-160d are at known or identical positions as the imageable body 104 relative to the base 102. The virtual points 160a-160d can correspond to the physical locations of the imageable portions 140a-140d of the imageable body 104 and also be referred to as virtual fiducial points 160a-160d. The virtual points 160a-160d can be aligned with the physical location of the imageable portions 140a-140d due to the keyed connection.

It will be understood, however, that the virtual points 160a-160d can simply be positioned with a known location relative to the physical location of the imageable portions 140a-140d when the tracking device 150 is interconnected with the base 102. The virtual points can be positioned at substantially the same location or any known location relative to the imageable portions 140a-140d. Further, because the virtual points 160a-160d each include a three dimensional location that is similar and/or known relative to the three dimensional location of the imageable portions 140a-140d, and because the tracking device 150 is fixed relative to the subject, position information with six degrees of freedom can be determined by tracking the tracking device 150.

Figure 5:
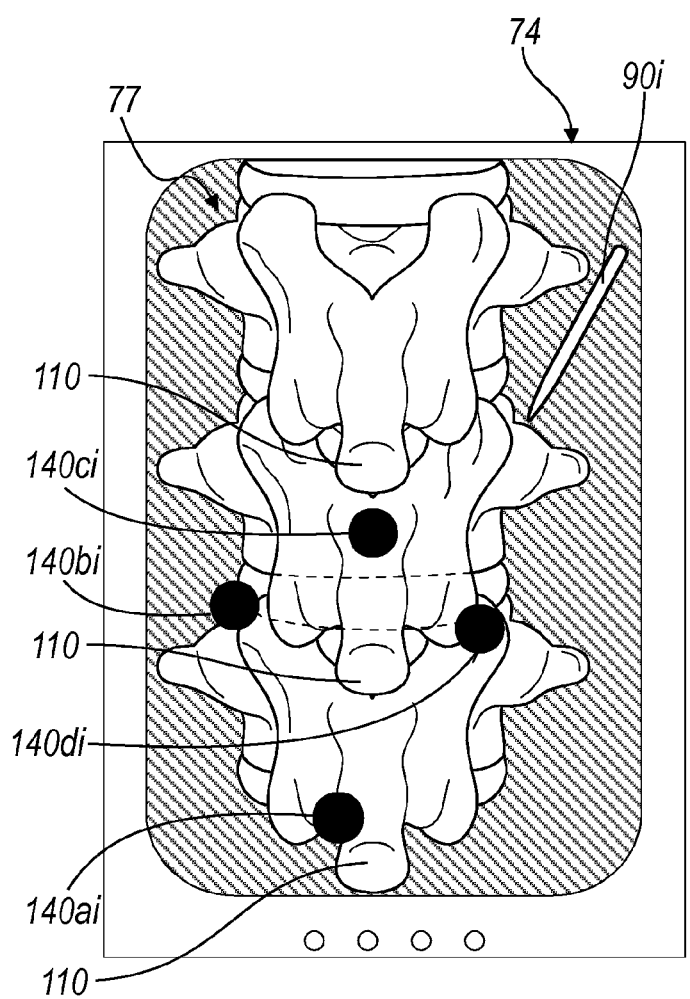
FIG. 5 is a diagram of image data.

With reference to FIG. 5, image data generated with an appropriate imaging device, can generate image data of the imageable body 104 to identify the imageable portions 140a-140d. The display 74 can include or display the image data 77 that includes images of the anatomy, such as the spinal process 110, and the imageable portions 140a-140d illustrated as points or dots 140ai-140di. The location of the points 140ai-140di in the image data can be used for registration, as discussed herein.

Figure 6:
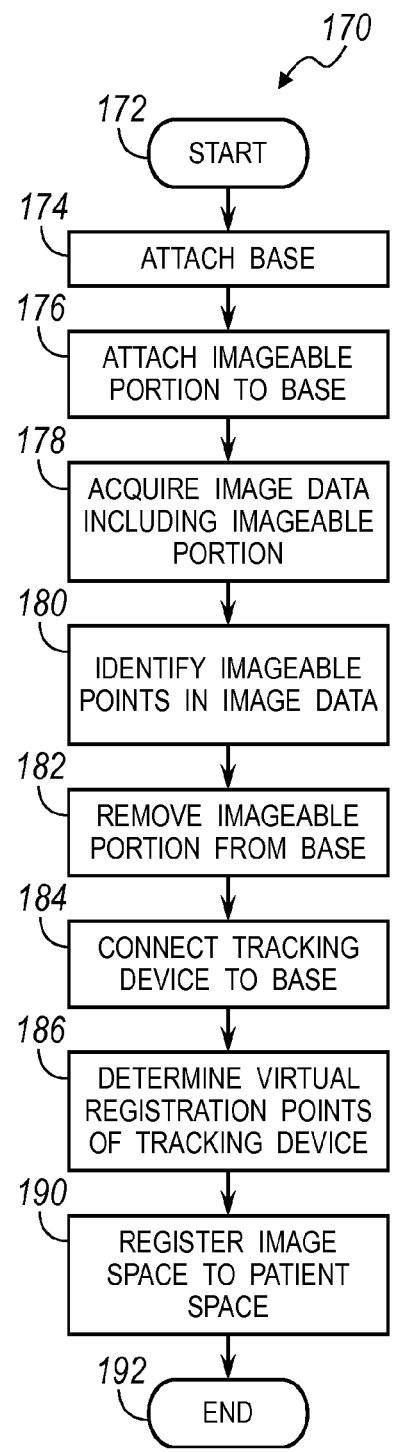
FIG. 6 is a flowchart of a method for registering image space to patient space.

With reference to FIG. 6, a method 170 is illustrated in a flow chart to acquire image data of the patient 14 and register the patient 14 to the image data 77, substantially automatically. With reference to FIG. 6, and continuing reference to FIGS. 1-5, the method can start in start block 172. The base 102 can be attached in block 174. The imageable body 104 can then be attached to the base in block 176. It will be understood, however, that the imageable body 104 can be incorporated with the base 102 prior to attachment of the base 102 or can be connected at any appropriate time. Further, the base 102 can be attached to any appropriate subject or portion of the subject, such as a spinal process 110.

Once the imageable body 104 and the base 102 are interconnected with the subject, image data can be acquired including the imageable body 104 in block 178. As discussed above, the image data can include any appropriate image data, such as an x-ray or CT or MRI, or any appropriate image data. Accordingly, the imageable portions 140a-140d of the imageable body 104 can be imageable with any appropriate or multiple imaging modalities. For example, the image data can be acquired using the O-Arm® imaging system, sold by Medtronic Navigation, Inc. having a place of business in Colo., USA. The imaging device can further include the imaging device disclosed in U.S. Pat. Nos. 7,188,998; 7,108,421; 7,106,825; 7,001,045; and 6,940,941, all incorporated herein by reference.

Once the image data has been acquired in block 178, the image points 140ai-140di, such as the points generated in the image data and by the imageable portions 140a-140d, can be identified in block 180. As illustrated in FIG. 5, the image points 140ai-140di can be generated in the image data 77. Accordingly, a program or system can be used to identify and locate the image points 140ai-140di. It will be understood that the image points 140ai-140di can be identified in any appropriate coordinate system. For example, it will be understood that the image points 140ai-140di can be identified in two, three, or four dimensions depending upon the image data acquired in block 178.

In identifying the imageable points 140ai-140di, the navigation system 10 or the user 81 can also identify the three dimensional coordinates in the image data that corresponds to the three dimensional coordinates of the imageable portions 140a-140d. Accordingly, the location of the image points 140ai-140di can be identified and located in the image data 77 in three dimensions. As discussed above, the location of the imageable points 140ai-140di can identify three dimensional points in the image data 77. Further, because the imageable body 104 is fixed to the base 102, which is further fixed to the subject, the image points 140ai-140di can be used to identify three dimensional locations, or a plurality of locations, in the image data relative to the subject.

The imageable body 104 can be removed from the base in block 182. The tracking device 150 can then be connected to the base in block 184. As discussed above, and illustrated in FIGS. 4A-4C, the tracking device 150 can be connected to the base 102 that is maintained in connection with the spinal process 110. Due to the connection, such as the keyed connection of the tracking device 150 with the base 102, the tracking device 150 can be positioned with a known location and orientation relative to the base 102. The fixation can be both axially and rotationally to assure a six degree of freedom tracking of the tracking device 150. Accordingly, connecting the tracking device 150 to the base 102 in block 184 can orient the tracking device 150 relative to the base 102 according to a known configuration and orientation. The known configuration can be known by the navigation system, such as by calling it from memory or entering data by the user 81. As further discussed above, the positioning of the tracking device 150 relative to the base 102 can allow the tracking device 150 to determine or transmit virtual coordinates in the navigation system 10.

Virtual fiducial points can be determined in block 186 and can be identifying or tracking the location of the virtual points 160a-160d with the tracking device 150. The virtual points 160a-160d, also referred to as virtual registration points, can be located in the navigation system 10, according to any known tracking modality. The virtual registration points 160a-160d can be identified in the subject space including the three dimensional coordinates of each of the virtual points. The identification of the virtual points can include identifying the tracking device 150 in the navigation system 10 to determine or input the calibrated or known location of the virtual points. As discussed above, the tracking device 150 can include the electromagnetic tracking sensor 152 that can be tracked with the electromagnetic localizer 84.

After identifying the image points 140ai-140di in the image data in block 180 and determining the virtual registration points 160a-160d of the tracking device in block 186, a registration of the image space to patient space can be made in block 190. Registration of the image space to the patient space can be performed because the identified image points 140ai-140di are in image space and the virtual fiducial points 160a-160d are defined by the tracking device 150 connected to the patient 14 in patient space. Accordingly, once the location of the image points 140ai-140di are identified in the image data in block 180, and the locations of the virtual fiducial points 160a-160d are identified in patient space in block 186, the registration can occur between the image space and the patient space. As discussed above, the locations of the virtual fiducial points 160a-160d in the subject space can be substantially identical to or at known locations relative to the physical locations of the imageable portions 140a-140d. Accordingly, the identical or known locations allow for registration as discussed further herein.

During registration, a translation map is determined between the image data coordinate system of the image data acquired in block 178 and the patient space defined by the patient 14. Once the registration occurs, the instrument 90 can be tracked with the tracking system that is registered to the image data to allow an identification and illustration of a position of the tracked instrument 90 as an icon superimposed on the image data. The registration procedure can then end in block 192.

Once the image data is registered to the patient space in block 190, tracking of the tracking device can occur according to any appropriate method or system, including those discussed above. Further, the method 170 can be carried out substantially automatically with a processor, such as the processor 72 of the workstation 73. The method 170 can be substantially automatic due to the identification of the image points 140ai-140di in the image data 180 and the determination of the virtual registration points 160a-160d of the tracking device 150 in block 186. Both of these determinations or identifications can be done substantially with a processor that is programmed or inputted with the calibrated data of the imageable portions 140a-140d and the virtual registration points 160a-160d. Accordingly, other than attaching the base 102, the imageable body 104, and the tracking device 150 to the patient 14, the user 22 need not interfere or participate in registration of the patient space to the image space and may efficiently prepare for a procedure, such as a spinal fusion, spinal implant procedure, or the like.

After the registration of the image space to the patient space in block 190, the instrument 90 can be tracked relative to the image data 77. As illustrated in FIG. 5, an icon 90i representing a location of the instrument 90 can be displayed relative to the image data 77 on the display 74. Due to the registration of the image space to the patient space, the position of the icon 90i relative to the image data 77 can substantially identify or mimic the location of the instrument 90 relative to the patient 14 in the patient space. As discussed above, this can allow a navigated procedure to occur.

After registering the image space to the patient space with a first image data set, subsequent image data sets can be acquired. Registration of the patient space to image space can be maintained without additional registration according to the flowchart 170 due to various controls or systems, such as robotic control systems.

For example, the imaging device 12 can know its location when the first image data set of the patient 14 is acquired. Because the imaging device 12 knows its location relative to the patient 12 when the first image data set is registered to the patient space, the registration also generates a known location of the imaging device 12 relative to the patient 14 due to the registration. Accordingly, additional or subsequent image data sets can be acquired of the patient 14 without requiring replacement of the imageable body 104. The position of the imaging device 12 relative to the patient 14 can be used to additionally register the new image data to the patient space. That is, the translation map generated when registering the image space to the patient space in block 190 can also translate the new position of the imaging device 12 relative to the patient 14 when acquiring a second or subsequent data set. Multiple image data sets can, therefore, be acquired of the patient 14 without requiring replacement of the imageable body 104 or further registration using the imageable portions 140a-140d. It will be understood that the imaging device can include the O-Arm® imaging device sold by Medtronic Navigation, Inc. including a robotic system or a position identification system that is operable to substantially precisely know the location of the imaging portions of the imaging device 12.

The imaging device 12, because it knows its location substantially precisely, can be used to register multiple image data sets taken sequentially or at any appropriate time. It will be understood, therefore, that the image data at a first time and a second time need not be separated by a portion of a procedure, but can be used to generate multiple image data sets of the patient 14 one substantially immediately after the other. For example, the imageable body 104 can connected to a portion of the patient 14 that is imaged during a first image data set acquisition time. A second image data acquisition can generate image data of a different portion of the patient 14, substantially immediately after acquiring a first image data set. However, the imageable body 104 need not be moved because the imaging device 12 knows its location during acquisition of the second image data set relative to the first image data set. Accordingly, once registration of the image data and image space to the patient space in block 190 occurs relating to the first image data set, registration of all the subsequent image data sets can be made relative to the image data set that includes the imageable body 104 and the imageable points 140ai-140di. It will be understood, however, the imageable body need not be present in the first or any particular data set. As long as the imageable body is present in one of the image data sets and the position of the imaging device is known for all of the image data sets, all of the image data sets can be registered.

Figure 7:
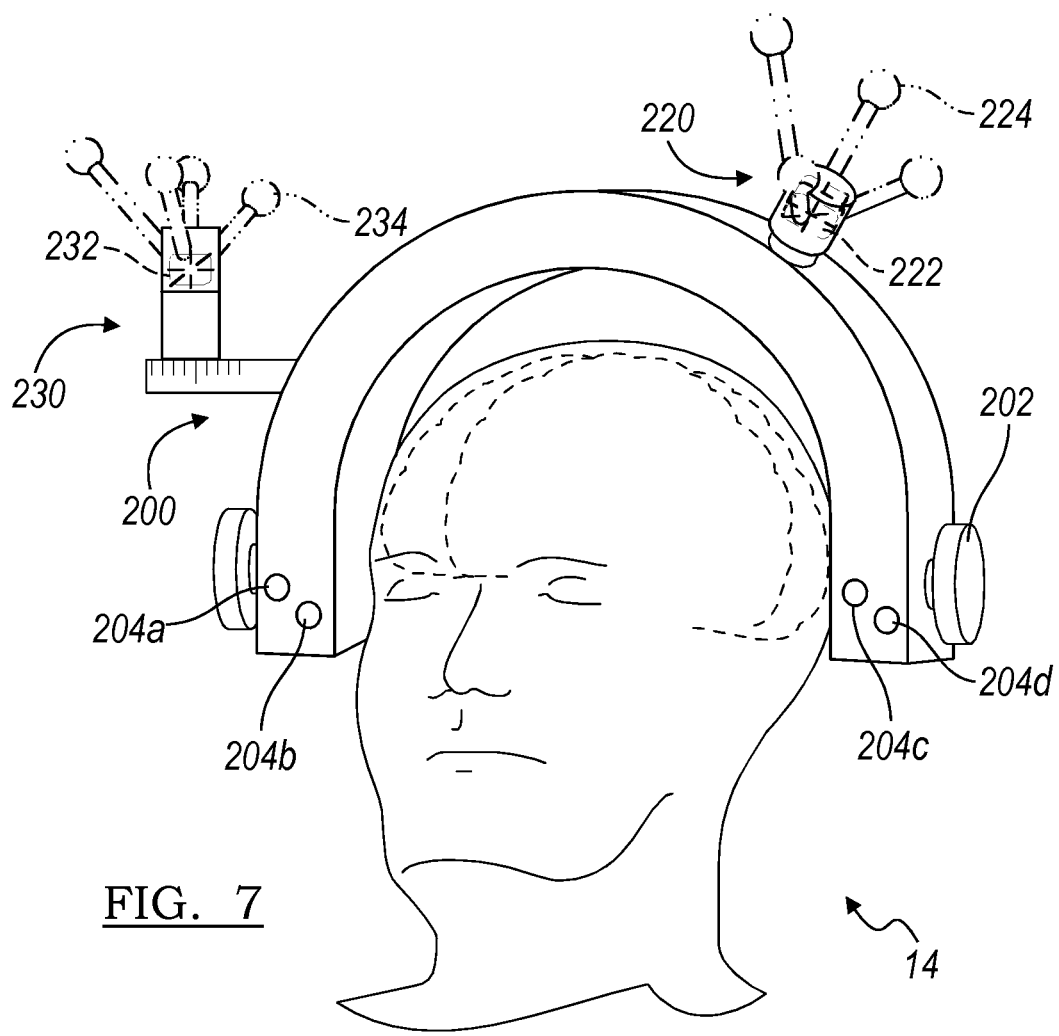
FIG. 7 is a plan view of a patient fixation device with imageable portions.

With reference to FIG. 7, a patient immobilization system 200, such as a Mayfield® clamp, can be connected to the patient 14. The patient immobilization system 200 can be connected to the patient 14 at any appropriate time, such as the prior to acquiring image data of the patient 14. The patient immobilization system 200 can be fixed to the patient 14 and be maintained fixed to the patient 14 during an entire operative procedure, as discussed further herein. The patient immobilization system 200 can be connected to the patient in any appropriate manner, such as with clamps, screws or other connection portions 202.

The patient fixation portion 200 can include a plurality of imageable portions, such as imageable portions 204a-204d. The imageable portions 204a-204d can be imaged with an imaging device, such as the imaging device 12, to generate or include image data that includes image points that represent the locations of the imageable portions 204a-204d. The imageable portions 204a-204d can be similar to the imageable portions 140a-140d, discussed above. The imageable portions 204a-204d included with the patient fixation device 200, therefore, can be imaged with any appropriate imaging system including those discussed above. The imageable portions 204a-204d can also have respective centers 204an-204dn that have three dimensional coordinates Xa, Ya, Za-Xd, Yd, Zd.

The position of the patient fixating device 200 can be determined in patient space with the tracking system, as discussed above. According to various embodiments, a calibration tracking device 220 can be connected to the patient fixation device 200. The calibration tracking device 220 can be tracked with any appropriate tracking system, such as with an EM tracking system via an EM tracking portion 222 or optical tracking system with an optical tracking portion 224. The EM tracking portion 222 or the optical tracking portion 224 can be included in a single device or be provided separately, and used with an appropriate tracking system.

The calibration tracking device 220 can be any appropriate device, such as the trackable tool to selectively touch portions or a trackable fixture that is separately connected with the patient fixation portion 200. According to various embodiments, the calibration tracking device 220 can include a keyed configuration that is positionable relative to the patient fixation device 200 in a selected orientation. A trackable tool (not illustrated) can touch several points to identify a location and orientation of the patient fixation device 200. Because the calibration fixture 220 can be keyed to the patient fixture 200 its orientation is known relative to the fixture 200 and the imageable portions 204a-204d. In addition, the patient fixation device 200 can transmit its location in the image data. For example, the patient fixation device 200 can include a member or device that can transmit to a magnetic resonance imager (MRI) its location within the image data to identify the location of the imageable portions 204a-204d.

When the calibration tracking device 220 is interconnected with the patient fixation portion 200, the navigation system 10 can know the location of the imageable portions 204a-204d in the patient space. This allows the navigation system to know the locations of the imageable portions 204a-204d that generates the image data points 204ai-204di, illustrated in FIG. 8, in the image data 77'. Once the location of the patient fixture 200 is known, the calibration fixture 220 can be removed. The image data 77' can be acquired with any appropriate image device, such as the imaging device is discussed above. Similarly the image data 77 can be displayed on the display 74 discussed above.

In addition to, or alternative to the calibration tracking device 220, a patient tracking device or dynamic reference frame (DRF) 230 can be interconnected with the patient fixation device 200. The dynamic reference frame 230 can be interconnected with the patient fixation device 200 to track motion of the patient 14 prior to and during an operative procedure. The DRF 230 is fixed to the fixation device 200 which is, in turn, fixed to the patient 14. Accordingly, movement of the patient 14 is translated through the patient fixation device 200 to the dynamic reference frame 230.

The dynamic reference frame 230 can be tracked with a tracking system, as discussed above, such as via an EM tracking portion 232 or one or more optical tracking portions 234. The DRF 230 can be used to maintain a registration of image space to patient space, as discussed above, in a navigation system. Accordingly, once registration occurs between the patient space of the patient 14 and image space of the image data, the DRF 230 can assist in maintaining the registration.

Figure 8:
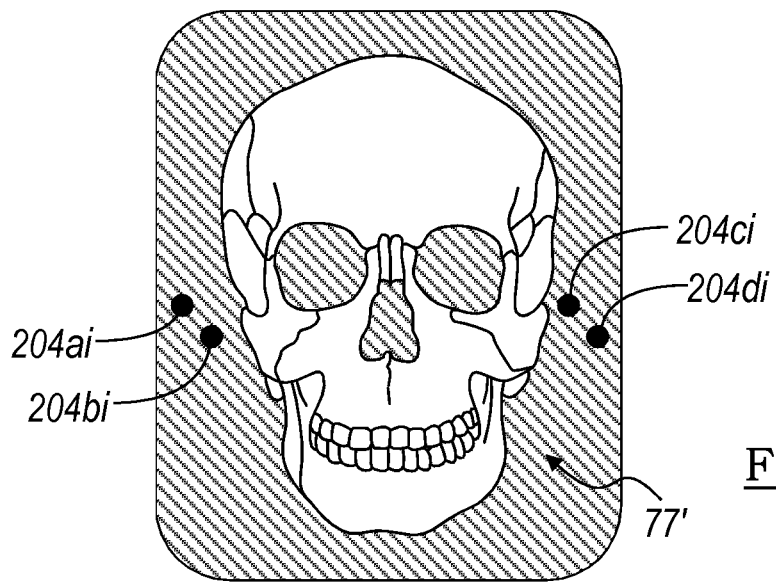
FIG. 8 is a diagram of image data.

In addition, the dynamic reference frame 230 can be tracked relative to the imageable portions 204a-204d. The imageable portions 204a-204d can be positioned at a fixed or selected location relative to the DRF 230. Because the DRF 230 is fixed to the patient fixation device 200, the location of the imageable portions 204a-204d can be known. Similarly, because the DRF 230 can be tracked with a tracking system, the physical location of the imageable portions 204a-204d can be known relative to the patient space of the patient 14. In addition, when the imageable points 204ai-204di are identified in the image data, as illustrated in FIG. 8, the image space location of the points can be translated to the physical location of the imageable portions 204a-204d.

According to various embodiments, the patient holder 200 that includes the imageable portions 204 and the two tracking devices 220 and 230 can be used and configured in selected variations. For example, the tracking device 220 affixed to the patient holder 200 can be used to determine the orientation of the imaginable portions 204 in patient space, as discussed above. The DRF 230 can then be attached to the patient holder 200 in any appropriate manner which can be moveable and selectively fixable, such as with locking clamps, relative to the patient 14. Accordingly, the navigation system 10 can take a single or initial snapshot to determine an orientation of the DRF 230 relative to the tracking device 220 and from this determine the orientation or position of the imageable portions 204 relative to the DRF 230. After the snapshot, at least one of the DRF 230 or the tracking device 220 can be removed from the patient holder 200. For example, if the tracking device 220 is not in a convenient location or would be covered with surgical draping, the tracking device 220 can be removed once the DRF 230 is fixed relative to the patient 14. In addition, it would be understood that the tracking device 220 can be positioned in a repeatable and removable manner. For example, a linkage system can be used to interconnect the tracking device 220 with the patient holder 200 such that the position of the tracking device 220 is known relative to the patient holder 200. Accordingly, the tracking device 220 can be used as the DRF 230 to position the tracing device 220 in the convenient location even with surgical draping. Accordingly, it will be understood that the patient holder 200 including the imageable portions 204 can be used with one or two tracking devices, such as the tracking device 220 and the DRF 230, as discussed above.

Registration of the image space and the image data 77 and patient space of the patient 14 can be performed substantially similarly as discussed in the method 170 illustrated in the flowchart in FIG. 6. The location of the imageable points 204ai-204di can be determined substantially automatically. Similarly, the known position of the physical location of the imageable portions 204a-204d can be known to either or both of the tracking devices 220, 230. Accordingly, the system can know the physical location of the imageable portions 204a-204d for registration to the image points 204ai-204di.

The base 102 or the patient fixation device 200 can be positioned or fixed relative to the patient 14 during a procedure. Appropriate bases or fixation portions can be fixed to any appropriate subject, such as a work piece, during a procedure or imaging of the subject. The imageable portions, either connected to or integrated with the base or fixation device, can be imaged in the image data. Because the tracking device, such as the tracking device 150, the calibration device 220, or the DRF 230, can be connected with the base or fixation device the location of the imageable portions on the base or fixation device can be known throughout the procedure. Accordingly, by maintaining fixation of the base 102 or the fixation device 200 to the patient or subject and tracking or knowing the location of the imageable portions in the subject space, a re-registration need not be performed. The registration can be maintained by maintaining a fixation of the base 102 or patient fixation device 200 to the patient 14. This can make a procedure more efficient by eliminating or reducing the need to register or identify locations of imageable portions in the image data 77.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of maintaining registration with a subject space, comprising:
    acquiring a first image data set by imaging a subject and an imageable portion with an imaging device;
    determining a first position of the imaging device during acquiring the first image data set;
    acquiring a second image data set of the subject without the imageable portion with the imaging device; and
    determining a second position of the imaging device during acquiring the second image data set relative to the determined position of the imaging device while acquiring the first image data set.

2. The method of claim 1, further comprising:
    controlling and saving the location of the imaging device during acquiring the first image data set and the second image data set.

3. The method of claim 2, further comprising:
    registering the subject space and the image space of the first image data set with use of the imageable portion; and
    correlating the registration with the determined first position of the imaging device.

4. The method of claim 3, further comprising:
    translating the registration of the subject space and the image space of the first image data to the acquired second image data set based on a comparison of the determined first position and the determined second position.

5. The method of claim 3, wherein the registering the subject space and the image space of the first image data set with use of the imageable portion, includes:
    determining the location of the imageable portion in the first acquired image data set;
    determining the location of the imageable portion in subject space; and
    determining a translation between the image space and the subject space based on both the determined the location of the imageable portion in the first acquired image data set and the determined location of the imageable portion in subject space.

6. The method of claim 5, further comprising:
    tracking an instrument;
    determining a location of the instrument in the subject space;
    displaying a position of the instrument superimposed on the image data based on the determined translation.

7. The method of claim 1, further comprising:
    sequentially acquiring with the imaging device, the first image data set by imaging the subject and the imageable portion and then acquiring the second image data set of the subject without the imageable portion.

8. The method of claim 3, wherein registering the subject space and the image space of the first image data set includes:
attaching the imageable portion to a base;
removing the imageable portion from the base after acquiring the first image data set; and
attaching a tracking device to the base.

9. The method of claim 8, further comprising:
wherein attaching the tracking device to the base includes orienting the tracking device relative to the base according to a known orientation.

10. The method of claim 9, further comprising:
tracking the tracking device; and
determining virtual fiducial points that relate to a location of the imageable portion when attached to the base.

11. The method of claim 10, further comprising:
identifying image points in the first image data set relating to the imageable portion.

12. A method of maintaining registration with a subject space, comprising:
acquiring a first image data set by imaging a subject having an imageable portion connected to the subject with at least an image capturing portion of an imaging device;
determining a first position of at least the image capturing portion of the imaging device during the acquisition of the first image data set;
acquiring a second image data set of the subject with the imaging device without the imageable portion connected to the subject; and
determining a second position of at least the image capturing portion of the imaging device during the acquisition of the second image data set relative to the determined first position of at least the image capturing portion of the imaging device while acquiring the first image data set.

13. The method of claim 12, further comprising:
sequentially acquiring with the imaging device, wherein acquiring the first image data set occurs prior to acquiring the second image data set of the subject without the imageable portion.

14. The method of claim 12, further comprising:
attaching the imageable portion to a base;
removing the imageable portion from the base after acquiring the first image data set; and
attaching a tracking device to the base.

15. The method of claim 14, wherein attaching the imageable portion to the base includes attaching the imageable portion with a keyed connection in the base at a first known orientation;
wherein attaching the tracking device to the base includes attaching the tracking device to the base with the keyed connection in a second known orientation.

16. The method of claim 15, further comprising:
tracking the tracking device; and
determining virtual fiducial points that relate to a location of the imageable portion when attached to the base.

17. The method of claim 16, further comprising:
identifying image points in the first image data set relating to the imageable portion.

18. The method of claim 17, further comprising:
registering the subject space and the image space of the first image data set at least with the identified image points and the determined virtual fiducial points.

19. The method of claim 18, further comprising:
correlating the registration with the determined first position of the imaging device.

20. A method of maintaining registration with a subject space, comprising:
acquiring a first image data set by imaging a subject and an imageable portion with at least an image capturing portion of an imaging device, wherein the imageable portion has a keyed connection to a base and the base is connected to the subject;
determining a first position of at least the image capturing portion of the imaging device during the acquisition of the first image data set;
registering a subject space of the subject and an image space of the first image data set at least with identified image points in the first image data set and a tracked location of a tracking device connected to the base with the keyed connection;
correlating the registration with the determined first position of the imaging device;
acquiring a second image data set of the subject with the imaging device without the imageable portion connected to the subject; and
determining a second position of at least the image capturing portion of the imaging device during the acquisition of the second image data set relative to the determined first position of at least the image capturing portion of the imaging device while acquiring the first image data set.

21. The method of claim 20, further comprising:
translating the registration of the subject space and the first image data set to the second image data set based on the determined second position of the image capturing portion of the imaging device during the acquisition of the second image data set relative to the determined first position of at least the image capturing portion of the imaging device while acquiring the first image data set.

* * * * *